United States Patent
Armstrong et al.

(10) Patent No.: US 8,478,420 B2
(45) Date of Patent: Jul. 2, 2013

(54) IMPLANTABLE MEDICAL DEVICE CHARGE BALANCE ASSESSMENT

(75) Inventors: Randolph K. Armstrong, Houston, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 1764 days.

(21) Appl. No.: 11/457,033

(22) Filed: Jul. 12, 2006

(65) Prior Publication Data
US 2008/0015641 A1    Jan. 17, 2008

(51) Int. Cl.
*A61N 1/08* (2006.01)
(52) U.S. Cl.
USPC .............................................................. 607/63
(58) Field of Classification Search
USPC ................................................ 607/46, 55–57
See application file for complete search history.

(56) References Cited

U.S. PATENT DOCUMENTS

| | | |
|---|---|---|
| 3,421,511 A | 1/1969 | Schwartz et al. |
| 3,760,812 A | 9/1973 | Timm et al. |
| 3,796,221 A | 3/1974 | Hagfors |
| 4,291,699 A | 9/1981 | Geddes et al. |
| 4,305,402 A | 12/1981 | Katims |
| 4,384,926 A | 5/1983 | Wagner |
| 4,407,303 A | 10/1983 | Akerstrom |
| 4,458,696 A | 7/1984 | Larimore |
| 4,459,989 A | 7/1984 | Borkan |
| 4,573,481 A | 3/1986 | Bullara |
| 4,590,946 A | 5/1986 | Loeb |
| 4,592,359 A | 6/1986 | Galbraith |
| 4,606,349 A | 8/1986 | Livingston et al. |
| 4,608,985 A | 9/1986 | Crish et al. |
| 4,612,934 A | 9/1986 | Borkan |
| 4,628,942 A | 12/1986 | Sweeney et al. |
| 4,630,615 A | 12/1986 | Yomtov |
| 4,649,936 A | 3/1987 | Ungar et al. |
| 4,702,254 A | 10/1987 | Zabara |
| 4,793,353 A | 12/1988 | Borkan |
| 4,821,724 A | 4/1989 | Whigham et al. |
| 4,827,932 A | 5/1989 | Ideker et al. |
| 4,850,356 A | 7/1989 | Heath |
| 4,860,616 A | 8/1989 | Smith |
| 4,867,164 A | 9/1989 | Zabara |
| 4,870,341 A | 9/1989 | Pihl et al. |

(Continued)

FOREIGN PATENT DOCUMENTS

WO    2004/069330    8/2004

OTHER PUBLICATIONS

J. Walter Woodbury and Dixon M. Woodbury, Vagal Stimulation Reduces the Severity of Maximal Electroshock Seizures in Intact Rates: Use of a Cuff Electrode for Stimulating and Recording, Department of Physiology, School of Medicine, University of Utah, Jan. 1991, pp. 94-107, vol. 14, Salt Lake City, Utah.

(Continued)

*Primary Examiner* — Allen Porter, Jr.
(74) *Attorney, Agent, or Firm* — Cyberonics, Inc.

(57) ABSTRACT

A method is provided including delivering at least one electrical signal to tissue of a patient through an electrode. The method further includes assessing whether a net charge remains on the electrode a predetermined period of time after the delivery of the electrical signal. Systems for delivering such a signal, and assessing whether a net charge remains on the electrode providing the signal, are also provided.

12 Claims, 3 Drawing Sheets

U.S. PATENT DOCUMENTS

| | | | |
|---|---|---|---|
| 4,899,750 A | 2/1990 | Ekwall | |
| 4,903,700 A * | 2/1990 | Whigham et al. | 607/13 |
| 4,920,979 A | 5/1990 | Bullara | |
| 4,964,407 A | 10/1990 | Baker, Jr. et al. | |
| 4,969,468 A | 11/1990 | Byers et al. | |
| 4,979,511 A | 12/1990 | Terry, Jr. | |
| 5,003,975 A | 4/1991 | Hafelfinger et al. | |
| 5,025,807 A | 6/1991 | Zabara | |
| 5,095,905 A | 3/1992 | Klepinski | |
| 5,111,815 A | 5/1992 | Mower | |
| 5,137,020 A | 8/1992 | Wayne et al. | |
| 5,137,021 A | 8/1992 | Wayne et al. | |
| 5,139,028 A | 8/1992 | Steinhaus et al. | |
| 5,146,920 A | 9/1992 | Yuuchi et al. | |
| 5,154,172 A | 10/1992 | Terry, Jr. et al. | |
| 5,179,950 A | 1/1993 | Stanislaw | |
| 5,186,170 A | 2/1993 | Varrichio et al. | |
| 5,188,104 A | 2/1993 | Wernicke et al. | |
| 5,201,808 A | 4/1993 | Steinhaus et al. | |
| 5,201,865 A | 4/1993 | Kuehn | |
| 5,205,285 A | 4/1993 | Baker, Jr. | |
| 5,215,086 A | 6/1993 | Terry, Jr. et al. | |
| 5,215,089 A | 6/1993 | Baker, Jr. | |
| 5,222,494 A | 6/1993 | Baker, Jr. | |
| 5,237,991 A | 8/1993 | Baker, Jr. et al. | |
| 5,251,634 A | 10/1993 | Weinberg | |
| 5,263,480 A | 11/1993 | Wernicke et al. | |
| 5,269,303 A | 12/1993 | Wernicke et al. | |
| 5,299,569 A | 4/1994 | Wernicke et al. | |
| 5,304,206 A | 4/1994 | Baker, Jr. et al. | |
| 5,330,515 A | 7/1994 | Rutecki et al. | |
| 5,335,657 A | 8/1994 | Terry, Jr. et al. | |
| 5,351,394 A | 10/1994 | Weinberg | |
| 5,411,528 A | 5/1995 | Miller et al. | |
| 5,431,692 A | 7/1995 | Hansen et al. | |
| 5,466,255 A | 11/1995 | Franchi | |
| 5,501,702 A | 3/1996 | Plicchi et al. | |
| 5,507,786 A | 4/1996 | Morgan et al. | |
| 5,522,865 A | 6/1996 | Schulman et al. | |
| 5,531,778 A | 7/1996 | Maschino et al. | |
| 5,534,018 A | 7/1996 | Wahlstrand et al. | |
| 5,540,730 A | 7/1996 | Terry, Jr. et al. | |
| 5,540,734 A | 7/1996 | Zabara | |
| 5,549,646 A | 8/1996 | Katz et al. | |
| 5,571,150 A | 11/1996 | Wernicke et al. | |
| 5,575,813 A | 11/1996 | Edell et al. | |
| 5,620,474 A | 4/1997 | Koopman | |
| 5,658,318 A | 8/1997 | Stroetmann et al. | |
| 5,690,681 A | 11/1997 | Geddes et al. | |
| 5,700,282 A | 12/1997 | Zabara | |
| 5,707,400 A | 1/1998 | Terry, Jr. et al. | |
| 5,713,936 A | 2/1998 | Staub et al. | |
| 5,741,311 A | 4/1998 | McVenes et al. | |
| 5,743,860 A | 4/1998 | Hively et al. | |
| 5,755,742 A | 5/1998 | Schuelke et al. | |
| 5,755,747 A | 5/1998 | Daly et al. | |
| 5,759,199 A | 6/1998 | Snell et al. | |
| 5,769,873 A | 6/1998 | Zadeh | |
| 5,796,044 A | 8/1998 | Cobian et al. | |
| 5,814,088 A | 9/1998 | Paul et al. | |
| 5,876,425 A | 3/1999 | Gord et al. | |
| 5,891,179 A | 4/1999 | Er et al. | |
| 5,897,577 A | 4/1999 | Cinbis et al. | |
| 5,916,239 A | 6/1999 | Geddes et al. | |
| 5,919,220 A | 7/1999 | Stieglitz et al. | |
| 5,928,272 A | 7/1999 | Adkins et al. | |
| 5,995,868 A | 11/1999 | Osorio et al. | |
| 6,035,237 A | 3/2000 | Schulman et al. | |
| 6,052,624 A | 4/2000 | Mann | |
| 6,073,050 A | 6/2000 | Griffith | |
| 6,104,956 A | 8/2000 | Naritoku et al. | |
| 6,154,678 A | 11/2000 | Lauro | |
| 6,171,239 B1 | 1/2001 | Humphrey | |
| 6,181,969 B1 | 1/2001 | Gord | |
| 6,208,902 B1 | 3/2001 | Boveja | |
| 6,212,431 B1 | 4/2001 | Hahn et al. | |
| 6,216,045 B1 | 4/2001 | Black et al. | |
| 6,259,951 B1 | 7/2001 | Kuzma et al. | |
| 6,269,270 B1 | 7/2001 | Boveja | |
| 6,304,787 B1 | 10/2001 | Kuzma et al. | |
| 6,317,633 B1 | 11/2001 | Jorgenson et al. | |
| 6,339,725 B1 | 1/2002 | Naritoku et al. | |
| 6,341,236 B1 | 1/2002 | Osorio et al. | |
| 6,393,325 B1 | 5/2002 | Mann et al. | |
| 6,400,988 B1 | 6/2002 | Gurewitsch | |
| 6,411,844 B1 * | 6/2002 | Kroll et al. | 607/5 |
| 6,418,348 B1 | 7/2002 | Witte | |
| 6,445,951 B1 | 9/2002 | Mouchawar | |
| 6,453,198 B1 | 9/2002 | Torgerson et al. | |
| 6,456,481 B1 | 9/2002 | Stevenson | |
| 6,473,653 B1 | 10/2002 | Schallhorn et al. | |
| 6,477,417 B1 | 11/2002 | Levine | |
| 6,490,486 B1 | 12/2002 | Bradley | |
| 6,505,074 B2 | 1/2003 | Boveja et al. | |
| 6,510,332 B1 | 1/2003 | Greenstein | |
| 6,529,774 B1 | 3/2003 | Greene | |
| 6,553,263 B1 | 4/2003 | Meadows et al. | |
| 6,556,868 B2 | 4/2003 | Naritoku et al. | |
| 6,587,719 B1 | 7/2003 | Barrett et al. | |
| 6,587,727 B2 | 7/2003 | Osorio et al. | |
| 6,600,956 B2 | 7/2003 | Maschino et al. | |
| 6,600,957 B2 | 7/2003 | Gadsby | |
| 6,606,523 B1 | 8/2003 | Jenkins | |
| 6,609,025 B2 | 8/2003 | Barrett et al. | |
| 6,620,186 B2 | 9/2003 | Saphon et al. | |
| 6,622,038 B2 | 9/2003 | Barrett et al. | |
| 6,622,041 B2 | 9/2003 | Terry, Jr. et al. | |
| 6,622,047 B2 | 9/2003 | Barrett et al. | |
| 6,648,823 B2 | 11/2003 | Thompson | |
| 6,658,294 B1 | 12/2003 | Zadeh et al. | |
| 6,662,053 B2 | 12/2003 | Borkan | |
| 6,671,556 B2 | 12/2003 | Osorio et al. | |
| 6,684,105 B2 | 1/2004 | Cohen et al. | |
| 6,687,538 B1 | 2/2004 | Hrdlicka et al. | |
| 6,690,974 B2 | 2/2004 | Archer et al. | |
| 6,711,440 B2 | 3/2004 | Deal et al. | |
| 6,718,203 B2 | 4/2004 | Weiner et al. | |
| 6,718,207 B2 | 4/2004 | Connelly | |
| 6,721,600 B2 | 4/2004 | Jorgenson et al. | |
| 6,721,603 B2 | 4/2004 | Zabara et al. | |
| 6,725,092 B2 | 4/2004 | MacDonald et al. | |
| 6,731,979 B2 | 5/2004 | MacDonald | |
| 6,745,077 B1 | 6/2004 | Griffith et al. | |
| 6,754,539 B1 | 6/2004 | Erickson et al. | |
| 6,757,566 B2 | 6/2004 | Weiner et al. | |
| 6,760,624 B2 | 7/2004 | Anderson et al. | |
| 6,760,625 B1 | 7/2004 | Kroll | |
| 6,760,628 B2 | 7/2004 | Weiner et al. | |
| 6,763,268 B2 | 7/2004 | MacDonald et al. | |
| 6,778,856 B2 | 8/2004 | Connelly et al. | |
| 6,792,316 B2 | 9/2004 | Sass | |
| 6,795,730 B2 | 9/2004 | Connelly et al. | |
| 6,795,736 B2 | 9/2004 | Connelly et al. | |
| 6,799,069 B2 | 9/2004 | Weiner et al. | |
| 6,804,557 B1 | 10/2004 | Kroll | |
| 6,819,954 B2 | 11/2004 | Connelly | |
| 6,819,958 B2 | 11/2004 | Weiner et al. | |
| 6,829,509 B1 | 12/2004 | MacDonald et al. | |
| 6,843,870 B1 | 1/2005 | Bluger | |
| 6,845,266 B2 | 1/2005 | Weiner et al. | |
| 6,850,805 B2 | 2/2005 | Connelly et al. | |
| 6,875,180 B2 | 4/2005 | Weiner et al. | |
| 6,901,290 B2 | 5/2005 | Foster et al. | |
| 6,906,256 B1 | 6/2005 | Wang | |
| 6,907,295 B2 | 6/2005 | Gross et al. | |
| 6,920,357 B2 | 7/2005 | Osorio et al. | |
| 6,925,328 B2 | 8/2005 | Foster et al. | |
| 6,944,489 B2 | 9/2005 | Zeijlemaker et al. | |
| 6,949,929 B2 | 9/2005 | Gray et al. | |
| 6,954,674 B2 | 10/2005 | Connelly | |
| 6,961,618 B2 | 11/2005 | Osorio et al. | |
| 6,985,775 B2 | 1/2006 | Reinke et al. | |
| 6,993,387 B2 | 1/2006 | Connelly et al. | |
| 7,006,859 B1 | 2/2006 | Osorio et al. | |
| 7,010,357 B2 | 3/2006 | Helfer et al. | |
| 7,013,174 B2 | 3/2006 | Connelly et al. | |
| 7,015,393 B2 | 3/2006 | Weiner et al. | |

| | | |
|---|---|---|
| 7,047,074 B2 | 5/2006 | Connelly et al. |
| 7,054,686 B2 | 5/2006 | MacDonald |
| 7,107,097 B2 | 9/2006 | Stern et al. |
| 7,123,013 B2 | 10/2006 | Gray |
| 7,171,166 B2 | 1/2007 | Ng et al. |
| 7,174,219 B2 | 2/2007 | Wahlstrand et al. |
| 7,212,869 B2 | 5/2007 | Wahlstrom et al. |
| 7,221,981 B2 | 5/2007 | Gliner |
| 7,239,924 B2 | 7/2007 | Kolberg |
| 7,289,856 B1 | 10/2007 | Karicherla |
| 7,584,004 B2 | 9/2009 | Caparso et al. |
| 2002/0072782 A1 | 6/2002 | Osorio et al. |
| 2003/0083726 A1 | 5/2003 | Zeijlemaker et al. |
| 2003/0195601 A1 | 10/2003 | Hung et al. |
| 2003/0208244 A1* | 11/2003 | Stein et al. ............... 607/48 |
| 2004/0015205 A1 | 1/2004 | Whitehurst et al. |
| 2004/0059396 A1* | 3/2004 | Reinke et al. ............ 607/60 |
| 2004/0127953 A1* | 7/2004 | Kilgore et al. ........... 607/46 |
| 2004/0147992 A1 | 7/2004 | Bluger et al. |
| 2004/0167583 A1 | 8/2004 | Knudson et al. |
| 2004/0172088 A1 | 9/2004 | Knudson et al. |
| 2004/0172092 A1* | 9/2004 | Greenberg et al. ....... 607/48 |
| 2004/0210291 A1 | 10/2004 | Erickson |
| 2005/0015128 A1 | 1/2005 | Rezai et al. |
| 2005/0016657 A1 | 1/2005 | Bluger |
| 2005/0055056 A1* | 3/2005 | Olson ..................... 607/5 |
| 2005/0107858 A1 | 5/2005 | Bluger |
| 2005/0154426 A1 | 7/2005 | Boveja et al. |
| 2005/0154435 A1 | 7/2005 | Stern et al. |
| 2005/0222642 A1 | 10/2005 | Przybyszewski et al. |
| 2005/0272280 A1 | 12/2005 | Osypka |
| 2006/0058597 A1 | 3/2006 | Machado et al. |
| 2006/0106430 A1 | 5/2006 | Fowler et al. |
| 2006/0167497 A1 | 7/2006 | Armstrong et al. |
| 2006/0173493 A1 | 8/2006 | Armstrong et al. |
| 2006/0184211 A1 | 8/2006 | Gaunt et al. |
| 2006/0224199 A1* | 10/2006 | Zeijlemaker ............... 607/11 |
| 2006/0253164 A1 | 11/2006 | Zhang et al. |
| 2006/0265025 A1 | 11/2006 | Goetz et al. |
| 2007/0027497 A1* | 2/2007 | Parnis ..................... 607/45 |
| 2007/0027498 A1* | 2/2007 | Maschino et al. ......... 607/45 |
| 2007/0027500 A1* | 2/2007 | Maschino et al. ......... 607/45 |
| 2007/0032834 A1 | 2/2007 | Gliner et al. |
| 2007/0060991 A1 | 3/2007 | North et al. |
| 2007/0073150 A1 | 3/2007 | Gopalsami et al. |
| 2007/0100392 A1* | 5/2007 | Maschino et al. ......... 607/45 |
| 2007/0142889 A1 | 6/2007 | Whitehurst et al. |
| 2007/0173902 A1* | 7/2007 | Maschino et al. ......... 607/45 |
| 2007/0179557 A1* | 8/2007 | Maschino et al. ......... 607/45 |
| 2007/0179579 A1 | 8/2007 | Feler et al. |
| 2007/0179584 A1 | 8/2007 | Gliner |
| 2007/0239210 A1* | 10/2007 | Libbus et al. ............. 607/2 |
| 2007/0239223 A1* | 10/2007 | Engmark et al. .......... 607/37 |
| 2008/0033503 A1 | 2/2008 | Fowler et al. |
| 2008/0046035 A1 | 2/2008 | Fowler et al. |
| 2008/0071323 A1 | 3/2008 | Lowry et al. |
| 2008/0200925 A1 | 8/2008 | Johnson |
| 2008/0215110 A1 | 9/2008 | Gunderson et al. |
| 2008/0255582 A1 | 10/2008 | Harris |
| 2009/0076567 A1 | 3/2009 | Fowler et al. |

OTHER PUBLICATIONS

Mesut Sahin, Improved Nerve Cuff Electrode Recordings with Sub-threshold Anodic Currents, IEEE Transactions on Biomedical Engineering, Aug. 1998, pp. 1044-1050, vol. 45, No. 8.

Peter J. Basser and Bradley J. Roth, New Currents in Electrical Stimulation of Excitable Tissues, Annu. Rev. Biomed. Eng. 2000, vol. 2, pp. 377-397.

* cited by examiner

IMPLANTABLE MEDICAL DEVICE CHARGE BALANCE ASSESSMENT

BACKGROUND

1. Technical Field

This disclosure relates generally to implantable medical devices, and more particularly to methods, apparatus, and systems for assessing charge imbalance in implantable medical devices.

2. Background Information

There have been many improvements over the last several decades in medical treatments for disorders of the nervous system, such as epilepsy and other motor disorders, and abnormal neural discharge disorders. One of the more recently available treatments involves the application of an electrical signal to a patient's tissue to reduce various symptoms or effects of such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification. Electrical signals may be applied to the vagus nerve by implanting an electrical device underneath the skin of a patient and electrically stimulating tissue, organ(s) or nerves of the patient. The system may operate without a detection system if the patient has been diagnosed with epilepsy, periodically applying a prophylactic series of electrical pulses to the vagus (or other cranial) nerve intermittently throughout the day, or over another predetermined time interval. Alternatively, the system may include a detection system to detect one or more physiological parameters associated with a disorder (e.g., changes in brain activity as evidenced by EEG signals). When the physiological parameter is detected, the electrical signal is then applied to a target body location in response.

Typically, implantable medical devices (IMDs) involving the delivery of electrical signals to, or the sensing of electrical activity in, body tissues (e.g., pacemakers for sensing and applying a signal to heart tissue, and vagus nerve stimulators for similarly sensing or applying a signal to a vagus nerve) comprise a pulse generator for generating the electrical signal and a lead assembly coupled at its proximal end to the pulse generator terminals and at its distal end to one or more electrodes that interface with the body tissue to which the signal is applied. As used herein "stimulation" refers to the application of an electrical signal to a target body tissue, regardless of the effect that signal is intended to produce.

In providing a stimulation signal to a target body tissue, a continuous or net charge at the electrode/tissue interface is undesirable. Because stimulation involves applying an electrical charge to body tissue, IMDs are required to ensure that the net charge at the electrode/tissue interface is approximately zero, i.e., that the stimulation is charge balanced. IMD manufacturers use output coupling capacitors between the output circuits of the pulse generator and the electrodes to block errant continuous direct current ("DC") and serve as "passive" charge balancing components for the electrical signals being applied to the tissue. Charge built up on the electrodes during stimulation is offset by use of these output coupling capacitors, and discharged when delivery of a portion of the electrical signal is completed—typically after delivery of an individual pulse in a pulsed electrical signal. A "discharge phase" may be observed for a period, for example, after a monophasic stimulation phase. The stimulation phase and the discharge phase taken together may be considered a charge-balanced pulse in a signal comprising a plurality of such pulses.

Additionally, some IMDs may employ additional "active" charge balancing to reduce (or eliminate altogether) the workload on the passive charge balancing components (i.e., the output coupling capacitors). For active charge balancing, a stimulation of opposite polarity is applied at the electrode/tissue interface in a second phase after the initial stimulation. In such IMDs, active stimulation is set "a priori" based upon the programmed stimulation therapy. For example, a 1 mA pulse of 500 μS would be actively charge balanced by an opposite-polarity pulse of equal charge ($Q=I*T$) such as 1 mA for 500 μS or 0.25 mA for 2 mS. Since active charge balancing schemes are setup "a priori," and without examination and assessment of the actual amount of net charge remaining on the electrodes, active charge balancing units may not account for system problems.

In many IMDs that deliver an electrical signal, two electrodes (i.e., one cathode and one anode) are used to deliver the signal. However, some IMDs, such as pain neurostimulators, deliver electrical signals through multiple electrodes (e.g., 3 or more electrodes), and given the dynamic variation associated with delivery of the electrical signal and electrode switching to deliver that signal, the likelihood of residual charge at any electrode/tissue interface is increased in multi-electrode IMDs.

The present disclosure is directed to assessing when an undesirable net charge exists on at least one electrode, and preferably on each, electrode of an IMD, despite passive or active charge balancing efforts, such as when the output capacitors have failed, or the stimulation therapy being delivered is driven too hard for the particular output capacitors used.

BRIEF SUMMARY

In accordance with various embodiments, a method is provided for assessing charge imbalance on the electrodes of an implantable medical device. The method includes delivering at least one electrical signal, such as an electrical pulse, to tissue of a patient through an electrode. The method further includes assessing whether a net charge remains on the electrode a predetermined period of time after the electrical signal.

Still further embodiments are directed to a system for assessing whether a net charge remains on the electrodes of an implantable medical device. The system comprises a current source and an electrode that delivers an electrical signal generated by the current source to body tissue of a patient. The system further includes a charge balancing unit coupling the current source and the electrode. Additionally, the system includes a charge balance determination unit that detects a net charge remaining on the electrode a predetermined period of time after the electrical signal is delivered.

The preferred embodiments described herein do not limit the scope of this disclosure.

NOTATION AND NOMENCLATURE

Certain terms are used throughout the following description and claims to refer to particular system components. As one skilled in the art will appreciate, IMD manufacturers may refer to a component or groups of components by different names. This document does not intend to distinguish between components or groups thereof that differ in name but not function. In the following discussion and in the claims, the terms "including" and "comprising" are used in an open-ended fashion, adn thus should be interpreted to mean "including, but not limited to . . . ."

BRIEF DESCRIPTION OF THE DRAWINGS

The disclosure may be understood by reference to the following description taken in conjunction with the accompanying drawings, in which like reference numerals identify like elements, and in which.

Figure 1:
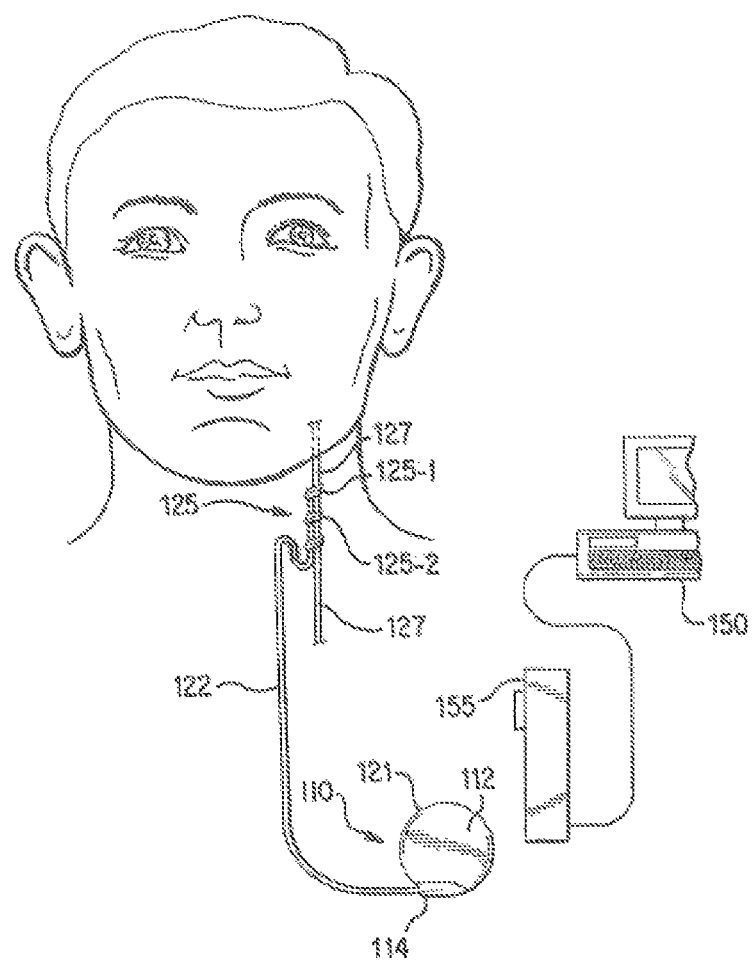
FIG. 1 is a stylized diagram of an implantable medical device suitable for use in the present disclosure implanted into a patient's body and an external programming device for programming the IMD.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION

Illustrative embodiments of the disclosure are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present disclosure provide methods and apparatus for assessing presence of a net charge on one or more electrodes of an implantable medical device. A more detailed description of an IMD suitable for use in the present disclosure is provided in various figures and the accompanying description below.

FIG. 1 illustrates an implantable medical device ("IMD") 110 having a main body 112 comprising a case or shell 121 with a header 114 for connecting to leads 122. The IMD 110 is implanted in the patient's chest in a pocket or cavity formed by the implanting surgeon just below the skin, similar to the implantation procedure for a pacemaker pulse generator. A nerve electrode assembly 125, preferably comprising an electrode pair, is conductively connected to the distal end of an insulated electrically conductive lead assembly 122, which preferably comprises a pair of lead wires (one wire for each electrode of an electrode pair). Lead assembly 122 is attached at its proximal end to the header 114 on case 121. The electrode assembly is surgically coupled to a vagus nerve 127, e.g. in the patient's neck (FIG. 1) or abdomen (not shown). The electrode assembly 125 preferably comprises a bipolar electrode pair, such as the electrode pair described in U.S. Pat. No. 4,573,481 issued Mar. 4, 1986 to Bullara. Persons of skill in the art will appreciate that many electrode designs could be used in the present disclosure. The two electrodes are preferably wrapped about the vagus nerve, and the electrode assembly 125 is preferably secured to the nerve 127 by a spiral anchoring tether such as that disclosed in U.S. Pat. No. 4,979,511 issued Dec. 25, 1990 to Reese S. Terry, Jr. and commonly owned by the assignee of the instant application. Lead assembly 122 may be secured, while retaining the ability to flex with movement of the chest and neck, by a suture connection to nearby tissue.

The IMD 110 may be controlled or programmed with an external programming device 150 (e.g., a desktop, laptop, or handheld computer, or a PDA) and a programming wand 155 to facilitate radio frequency (RF) communication between the external programming device 150 and the IMD 110. The wand 155 and software permit noninvasive communication with the IMD 110 after the latter is implanted.

Figure 2:
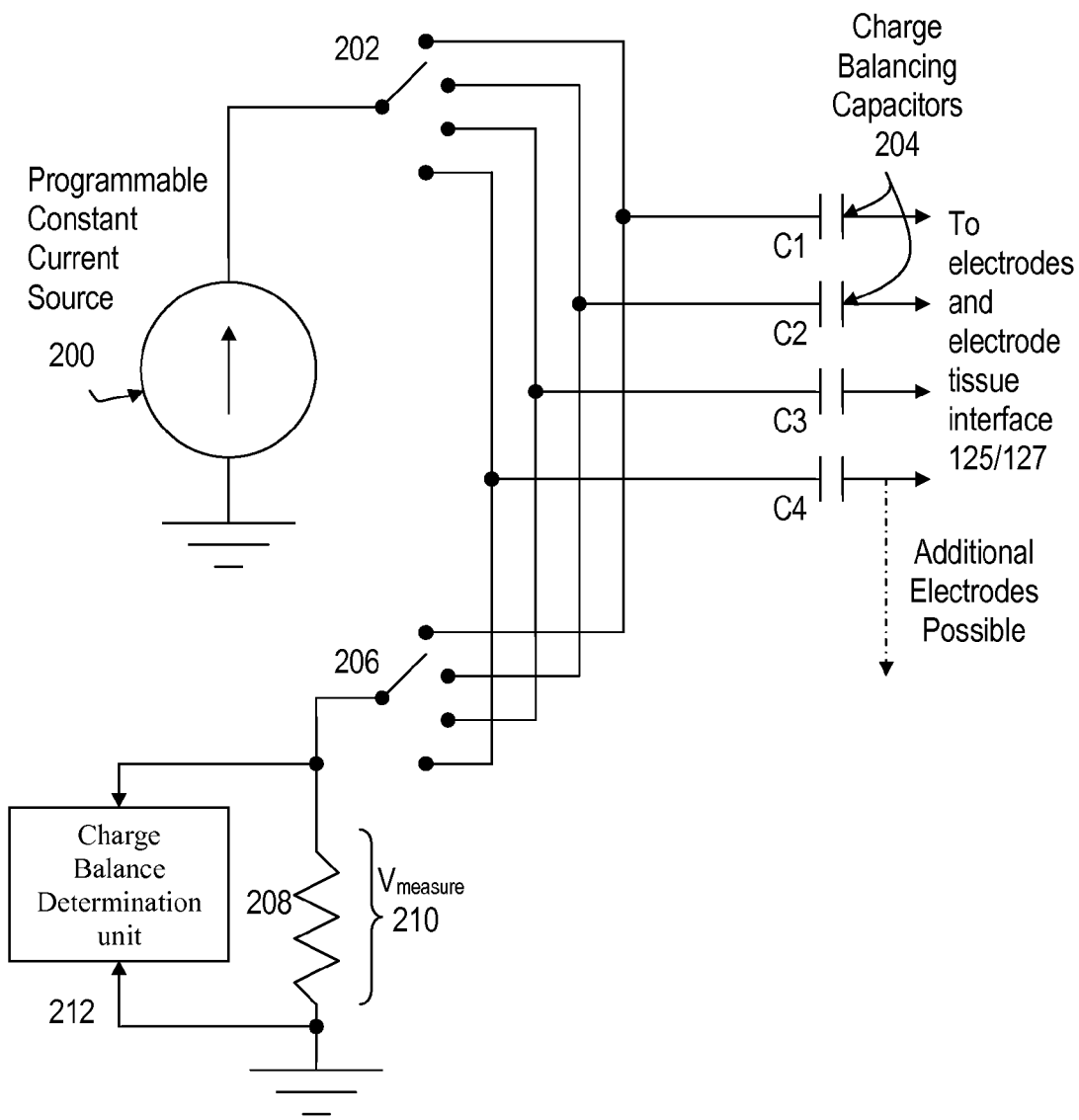
FIG. 2 is a circuit diagram of an embodiment of the present disclosure for charge imbalance assessment.

FIG. 2 illustrates a circuit diagram of an embodiment of the IMD 110 in greater detail. In various embodiments, the IMD 110 comprises a current source 200 that generates electrical stimulation pulses delivered to target tissue of the patient when switch 202 and switch 206 are closed to complete a circuit through the charge balancing capacitors (C1-C4) 204 and to the electrodes 125. Where the IMD is a neurostimulation device, the current source may comprise a constant current source, such as a programmable constant current source. Alternatively, the current source may comprise a constant voltage source where the IMD is a pacemakers or a defibrillator. In one embodiment, switches 202 and 206 may be synchronized to select a desired electrical signal path, e.g., switch 202 may select a first electrode as a cathode and switch 206 may selected a second electrode as an anode, thus defining, together with the target tissue of the patient, an electrical signal path. Any number of electrodes may be used individually or collectively as cathodes and/or anodes in the system, and the IMD 110 programming selects an output electrode (i.e., the cathode) using switch 202, and a return electrode (i.e., the anode) using switch 206. Persons of skill in the art will appreciate that multiple switches 202 or 206 may be provided where multiple electrodes are simultaneously used as a collective cathode or anode, respectively.

The charge balancing capacitors 204 (C1-C4) couple each respective electrode 125 to the switched circuitry to block errant continuous direct current and, when functioning properly as designed and not subject to too intense an electrical signal, discharge any charge built up on the electrodes 125 during application of the electrical signal to the electrodes and the tissues of the patient. For example, electrode 125-1 may be connected to C1, electrode 125-2 may be connected to C2, and housing 112 may be connected to C3. A fourth electrode (not depicted in FIG. 1), may also be connected to capacitor C4. During the application of a therapeutic electrical signal in such an example, switch 202 would connect current source 200 to charge balancing capacitor C1 and switch 206 would connect to charge balancing capacitor C2, producing a therapeutic electrical signal through electrodes 125-1 and 125-2. In at least some embodiments, the charge balancing capacitors are passive charge balancing components. By comparison, the circuitry may optionally comprise an active charge balancing unit (not shown) to reduce the workload on the charge balancing capacitors (or replace them altogether) by applying a second electrical signal of opposite polarity after the initial electrical signal is applied to tissue. In one embodiment, the active charge balancing unit comprises a current source.

Following delivery of the electrical signal, switches 202 and 206 may thereafter be used to assess whether an appreciable, undesirable net charge is present on an electrode. As referred to herein, assessing charge remaining on an electrode involves taking an actual measurement of the circuitry from which charge may be estimated or calculated based on other known system values, such as resistance, capacitance, voltage, and the like. In one embodiment, switch 202 may be left open or unconnected, and switch 206 may be connected to one of a plurality of electrodes for which assessment of the presence (or absence) of a net charge is desired. A resistor 208 is coupled to the output coupling capacitors via switch 206 and to ground. As shown in FIG. 2, the resistor 208 may, in one embodiment, be coupled to the proximal side (i.e., the same side as the current source 200) of the capacitors 204. In alternative embodiments, the resistor 208 may be coupled to the distal side of the capacitors 204, and in a still further embodiment, the resistor 208 may be coupled to both sides of the capacitors 204. The resistor 208 may be any value suitable for measuring voltage. If the resistor remains in path during delivery of the therapeutic electrical signal (i.e., both switches 202 and 206 are closed), resistor 208 should be small enough so as not to impede current delivery and waste energy. In certain embodiments (not shown), the resistor 208 is out-of-circuit during application of the therapeutic electrical signal to the electrodes 125, and therefore may be of relatively high impedance during the net charge assessment measurement. In one embodiment, resistor 208 is implemented with a value of 100 k ohms, although many variations on impedance are contemplated within the scope of this disclosure. A voltage differential 210 across the resistor 208 is measured by a charge balance determination unit 212, and used to estimate any existing net charge on the electrode. In one embodiment, the charge balance determination unit includes a voltage meter to measure the voltage differential 210 across the resistor 208.

Alternatively, in contrast to a voltage differential between a capacitor and ground, the charge balance determination unit 212 may sample the voltage differential 210 on the charge balancing capacitor 204 relative to another of the capacitors, or relative to a common conductor (such as the can 121). As previously noted, the charge balance determination unit 212 may sample voltage differential 210 using 1) the proximal side of the capacitors 204 (C1-C4) relative to the programmable constant current source, 2) the distal side, or 3) both sides of the capacitor. The voltage differential 210 may then be used by the charge balance determination unit 212 or the external programming device 150 to estimate any existing net charge balance on the electrode.

If the voltage differential 210 is equal to zero volts, there is no undesirable net charge remaining on the electrode(s). If the voltage differential 210 is greater than zero volts, net charge remains on the electrode(s), indicating that an undesirable condition may exist on the electrode(s) or the stimulated tissue. Alternatively, a voltage threshold may be set at an appropriately low value, sufficient to avoid undesirable conditions, such as 0.3 mV for a 100 nA current limit into a 3000 ohm lead. The voltage differential 210 may be compared to the voltage threshold to determine whether an undesirable net charge remains on the electrode. In such embodiments, such a voltage threshold may be adjusted according to the known lead impedance of the electrode. In order to implement a safety margin, the voltage threshold may be set lower than necessary to avoid an undesirable condition.

In various embodiments, the measurement of the voltage differential 210 by the charge balance determination unit 212 may be performed instantaneously. Alternatively, the voltage differential 210 may be evaluated over time. In general, no electrical signal is provided when measuring voltage differential 210 to check for a charge imbalance. The presence (or absence) of a net charge may simply be measured during the period following application of a regular therapeutic electrical signal. In one embodiment, the measurement by the charge balance determination unit 212 may be performed at routine intervals, such as once every hour, once every 24 hours or the like, to generate a response, such as an indicator or flag, the next time that the external programming device 150 communicates with the IMD 110.

The charge balance determination unit 212 may perform various activities based on the differential voltage 210 which is measured after the discharge phase of the capacitors (or the active charge-balancing signal, where active charge-balancing is employed) has ended. In an embodiment, the charge balance determination unit 212 converts the voltage differential 210 to net charge, and may either report the amount of the net charge on the electrodes to the external programming device 150 or store the net charge value, with a time-stamp, for later reporting. The IMD 110 may, in some embodiments, adjust the delivered electrical signal to reduce net charge without user input or programming from external programming device 150. In an alternative embodiment, the charge balance determination unit 212 transmits the voltage differential 210 to the external programming device 150, and the external programming device 150 may display a response and/or reprogram the IMD 110 as needed to reduce net charge on the electrode. In a further alternative embodiment, the IMD 110 may adjust the delivered therapeutic electrical signal to reduce net charge on the electrode without immediately reporting the adjustment to the external programming device 150.

In still another alternative embodiment, the charge balance determination unit 212 and/or the external programming device 150 may use the voltage differential 210 as a proxy for a measurement of net charge on the electrodes, and thus the generated response is a result of the comparison of the measured voltage to a threshold value, which may be programmably or otherwise predetermined. Such an embodiment provides a simplified alternative having a lower calculation burden on the IMD than previously described embodiments in which the measured voltage differential is converted to net charge.

Once an assessment of net charge and/or voltage differential 210 has been made, a response may be generated by a response module (not shown), which may generally be located either in the charge balance determination unit 212, in another part of the IMD 110 operatively connected to the charge balance determination unit 212, or in the external programming device 150. The response may include, for example, a patient notification or a physician notification generated on the display of the external programming device 150. Such a notification may be a sensory, textual or graphical alert that a charge imbalance has been detected, and the patient may notify the physician, or the physician may use the information to alter the delivered therapy or schedule surgery to replace the IMD 110, the electrodes 125, or both. A response may also include a change in the therapeutic electrical signal to be delivered, implemented without interaction by a patient or physician, such as a reduction in one or more parameters defining the electrical signal that is delivered (i.e., reducing the duration or intensity of the signal), an increase in active charge balancing (i.e., increasing the duration or intensity of a charge balancing signal), a modification to the signal path (i.e., by switching which electrodes among a plurality of electrodes are used to deliver the electrical signal), and disabling the stimulation entirely.

In multi-electrode stimulators, the techniques of the present disclosure are particularly valuable given that the dynamic variation of stimulation and electrode switching result in an increased likelihood of residual net charge remaining on the electrodes. The assessment of charge imbalance in a multi-electrode pulse generator may be performed by comparing the differential voltage for multiple electrodes with respect to one another or with respect to a common conductor (such as, in various embodiments, the can 121).

The presently disclosed method of detecting net charge and assessing charge imbalance may be implemented entirely in the IMD 110 in various embodiments, or alternatively, in a combination of the IMD 110 and the external programming device 150.

Utilizing embodiments of the present disclosure, an accurate assessment of the function and operation of the charge balancing circuitry may be performed, thereby providing better warnings to the user and/or to a healthcare provider assessing the operations of the IMD 110.

Figure 3:
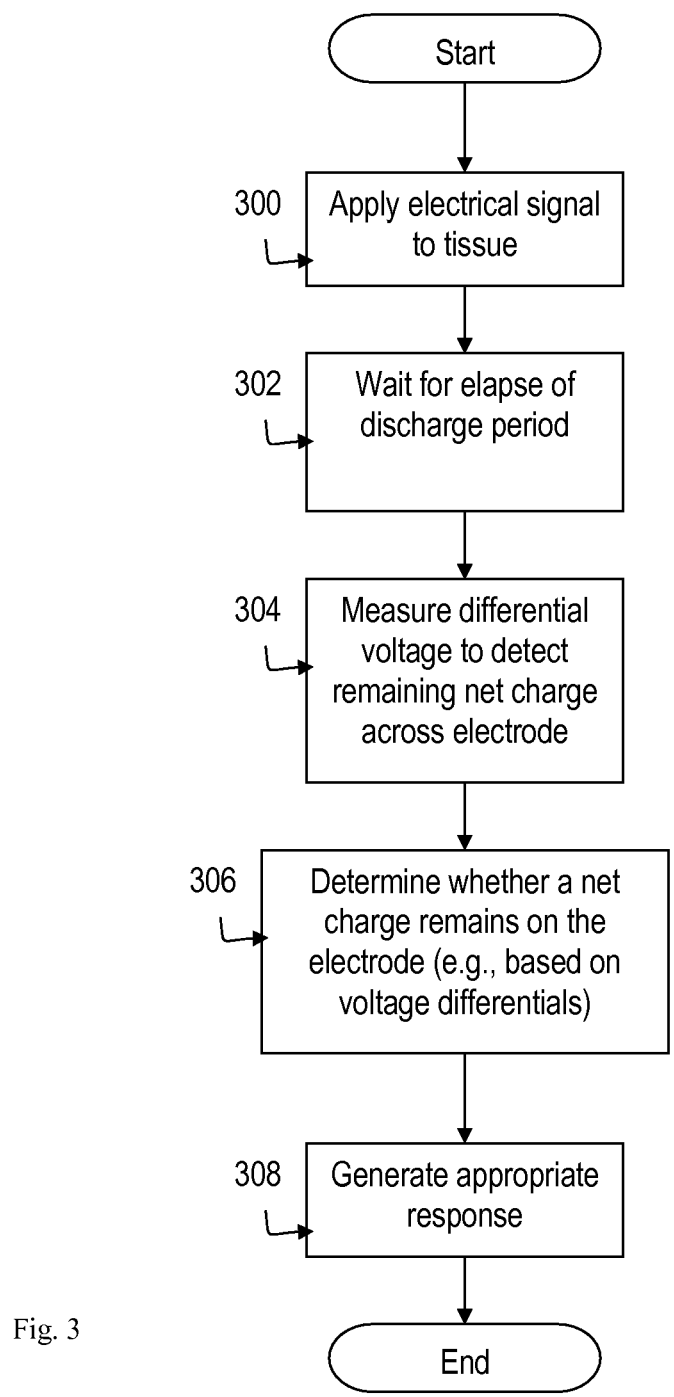
FIG. 3 is a flowchart representation of a method of assessing the presence of a net charge balance on an electrode of an IMD, in accordance with one illustrative embodiment of the present disclosure.

FIG. 3 is a flowchart of a method of assessing the presence or absence of a net charge in accordance with an embodiment of the present disclosure. The method begins as the IMD 110 applies an electrical signal to tissue (block 300). Specifically, in an embodiment, a therapeutic electrical signal is delivered by selecting an output electrode (one of electrodes 125) with switch 202 and a return electrode (another of electrodes 125) with switch 206. After delivery of the electrical signal is complete, a discharge period for the electrode may be provided, in which any residual charge on an electrode is drained to ground. In one embodiment of this discharge period, after application of the therapeutic electrical signal, switch 206 is switched to the same electrode as switch 202, and switch 202 is then opened.

Because the charge balancing unit is designed to effectively discharge any net charge remaining on the electrode within a predetermined period of time (i.e., the discharge period), in block 302 the method includes waiting until the discharge period has elapsed. The length of time for the discharge period may be a characteristic of the particular capacitors used in passive charge balancing or the minimum amount of time necessary to apply an active charge balancing, opposite polarity electrical signal to the electrode. More generally, a "predetermined period of time" can be any time period subsequent to the completion of delivery of the electrical signal, and desirably is a sufficient time thereafter to permit all (or nearly all) residual electrical charge to drain from the electrode 125 to ground. The period may be predetermined by a user, the external programmer 150, or one or more subsystems within the IMD 110 itself. The drainage characteristics for the electrode 125 will be known, depending upon such parameters as whether active or passive charge balancing is used, the circuit components, the amplitude and duration of the therapeutic electrical signal, and other factors known to persons of skill in the art. In particular, the period may constant or variable, and may be shorter than or longer than the complete discharge period for the residual charge, as long as the measured value of residual charge is interpreted and compared with regard to the charge expected to remain on the electrode based upon the known parameters and period of time used for that measurement.

In block 304, the method includes measuring a voltage differential 210 to detect whether any net charge remains on the electrode after the discharge period has elapsed. Specifically, in an embodiment, switch 206 is switched to any desired electrode in order to see if any net charge remains on that electrode by evaluating the voltage differential 210. In one embodiment, the method includes detecting residual net charge remaining on the electrode by measuring an instantaneous voltage differential 210 on the proximal side of the charge balancing capacitor. Alternatively, wires on the distal side of the capacitor may be the inputs to switch 206 such that the method includes detecting residual charge on the electrode by measuring the instantaneous voltage differential 210 at the distal side of the capacitor.

In block 306, the method includes determining whether a remaining net charge is present across the electrode based on the measured differential voltage 210. The residual voltage (measured as voltage differential 210) on a capacitor after a predetermined period should be no more than the amount of current that will result in an undesirable condition times the electrode/tissue resistance $R_e$ at the electrode (i.e., $V=T*R_e$). In one embodiment, 100 nA is a threshold limit on current after the discharge period for the capacitors. While charge is not directly measured, it may be calculated from the direct measurement of voltage differential 210 as $C*V_{measure}$, where C is the capacitance of the charge balancing capacitor 204, and $V_{measure}$ is the measured voltage differential 210. In one illustrative implementation, $R_e$ would be 3000 ohms, so the voltage threshold would be 0.3 mV. For a 10 µF coupling capacitor, the limit on tolerable net charge would equate to 3 nCoulombs.

An appropriate response is generated based on whether a net charge exists across the electrode (block 308). In certain embodiments, the response may be determined by the magnitude of the net charge. As noted previously, an appropriate response may range from doing nothing if no charge remains on the electrode to notification of either the patient or the physician, to changing the electrical signal delivered. Specifically, an appropriate response could be reducing the therapeutic electrical signal that is delivered such that the electrode is not driven as hard, increasing the active charge balancing electrical signal if used, modifying the stimulation path used in delivering the therapeutic electrical signal (i.e., by switching which electrode of a plurality of electrodes is used to deliver the signal), or disabling the therapeutic electrical signal entirely, such as until the charge balancing capacitors and/or electrode can be surgically replaced.

The particular embodiments disclosed above are illustrative only, as the disclosure may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the disclosure. Accordingly, the protection sought herein is as set forth in the claims below.

What is claimed is:

1. A method for charge balance assessment in an implantable medical device, the method comprising:
    delivering, via a current source, at least one electrical signal to tissue of a patient through an electrode; and
    assessing, via a charge balance determination unit, whether a net charge remains on the electrode a predetermined period of time after the delivery of the electrical signal;
    wherein said predetermined period of time is at least one hour.

2. The method of claim 1, wherein assessing whether a net charge remains on the electrode comprises measuring a voltage differential between a charge balancing capacitor associated with the electrode and a reference voltage, and estimating the net charge remaining based on the measured voltage differential.

3. The method of claim 2, wherein measuring the voltage differential comprises measuring a voltage differential across a resistor coupled to a charge balancing capacitor associated with the electrode and a reference voltage, and estimating the charge balance based on the measured voltage differential.

4. The method of claim 2, wherein measuring the voltage differential between a charge balancing capacity and a reference voltage comprises measuring said differential from at least one of:
   a) the proximal side of the charge balancing capacitor; and
   b) the distal side of the charge balancing capacitor.

5. The method of claim 2, wherein said reference voltage is selected from the group consisting of:
   a) another electrode;
   b) a common conductor of the implantable medical device; and
   c) ground.

6. The method of claim 2, wherein said reference voltage is selected from the group consisting of:
   a) another electrode; and
   b) a common conductor of the implantable medical device.

7. The method of claim 1, further comprising generating a response based on the step of assessing whether a net charge imbalance remains on the electrode.

8. The method of claim 7, wherein generating a response comprises at least one of:
   a) generating a notification to one of the patient and a physician that a net charge remains on the electrode when the predetermined period of time has elapsed;
   b) changing the electrical signal delivered by the electrode;
   c) modifying a path by which the electrical signal is delivered such that an electrode other than the electrode carrying a net charge is used for delivering the electrical signal;
   d) disabling delivery of the electrical signal by way of the electrode carrying a net charge;
   e) switching from passive charge balancing to active charge balancing; and
   f) increasing the active charge balancing to eliminate the net charge.

9. The method of claim 7, wherein generating a response comprises at least one of:
   a) generating a notification to one of the patient and a physician that a net charge remains on the electrode when the predetermined period of time has elapsed;
   b) disabling delivery of the electrical signal by way of the electrode carrying a net charge; and
   c) switching from passive charge balancing to active charge balancing.

10. The method of claim 1, wherein delivering at least one electrical signal comprises delivering said at least one electrical signal via a plurality of electrodes, and the method further comprising assessing whether a net charge remains on each of said plurality of electrodes.

11. The method of claim 1, further comprising selecting at least one electrode from among a plurality of electrodes through which to deliver the at least one electrical signal to tissue, and assessing whether a net charge remains on each said selected electrode.

12. The method of claim 1, further comprising transmitting from the implantable medical device to an external programming device a signal indicative of whether a net charge remains on the electrode.

* * * * *